US00PP26299P3

(12) United States Plant Patent
Eremin

(10) Patent No.: US PP26,299 P3
(45) Date of Patent: Jan. 12, 2016

(54) ***PRUNUS* ROOTSTOCK PLANT NAMED 'AP3'**

(50) Latin Name: ***(Prunus pumila* L.×*P. salicina* Lindl.)×*P. cerasifera Ehrh.***
Varietal Denomination: AP3

(75) Inventor: Gennadiy Eremin, Krasnodar Region (RU)

(73) Assignee: Krymsk Experimental Breeding Station, Krasnodar Region (RU)

( * ) Notice: Subject to any disclaimer, the term of this patent is extended or adjusted under 35 U.S.C. 154(b) by 237 days.

(21) Appl. No.: 13/507,760

(22) Filed: Jul. 26, 2012

(65) Prior Publication Data

US 2014/0033376 P1 Jan. 30, 2014

(51) Int. Cl.
*A01H 5/06* (2006.01)
*A01H 5/08* (2006.01)

(52) U.S. Cl.
USPC ..... Plt./180
CPC ..... *A01H 5/0837* (2013.01)

(58) Field of Classification Search
USPC ..... Plt./184, 183, 180
See application file for complete search history.

(56) References Cited

U.S. PATENT DOCUMENTS

| | | | | |
|---|---|---|---|---|
| PP11,233 P * | 2/2000 | Jacob | Plt./183 |
| PP16,114 P3 * | 11/2005 | Eremin | Plt./183 |
| PP21,432 P2 * | 11/2010 | Pinochet | Plt./183 |
| PP23,631 P2 * | 5/2013 | Bliss et al. | Plt./183 |

* cited by examiner

*Primary Examiner* — Anne Grunberg
(74) *Attorney, Agent, or Firm* — The Webb Law Firm

(57) ABSTRACT

A new and distinct (*Prunus pumila* L.×*P. salicina* Lindl.)×*P. cerasifera* Ehrh. plant used as a rootstock for many different varieties that exhibits desirable disease resistance.

8 Drawing Sheets

Botanical classification: (*Prunus pumila* L.×*P. salicina* Lindl.)×*P. cerasifera* Ehrh.

Varietal denomination: 'AP3'.

BACKGROUND OF THE INVENTION

The present invention comprises a new and distinct cultivar of (*Prunus pumila* L.×*P. salicina* Lindl.)×*P. cerasifera* Ehrh. used as a rootstock known by the varietal name 'AP3'. The new variety was discovered at a breeding station in the town of Krymsk in the Krasnodar region of Russia in 1999. The new variety is the result of planned breeding between a *Prunus pumila*×*P. salicina* plant named 'Sapa' (female parent, unpatented) and a *Prunus cerasifera* plant named 'Otlichnitsa' (male parent, unpatented). The purpose of breeding 'AP3' was to provide a productive and adaptive rootstock with a dwarf-like growth habit. The new variety is perfectly compatible with peach, apricot, and plum varieties. The new variety is a different species than both parents, but is a species of the *Prunus* genus. When compared to 'Sapa', 'AP3' exhibits similar juicy fruit flesh, numerous flowers, and non-branching shoots. When compared to 'Otlichnitsa', 'AP3' exhibits juicier fruit flesh and more flowers. Further, the shoots of 'AP3' do not branch, while the shoots of 'Otlichnitsa' branch out.

When compared to *Prunus* rootstock 'Marianna 4001' (unpatented), 'AP3' is similar in growth habit, propagation by cuttings, and high productivity of grafted varieties. It differs from 'Marianna 4001' in low temperature tolerance and weak branching habit of shoots.

The new variety has been trial and field tested and has been found to retain its distinctive characteristics and remain true to type through successive propagations. The following characteristics generally distinguish 'AP3' from other varieties known to the breeder:

1. 'AP3' exhibits medium vigor;
2. Rooting can be done by cuttings or layering;
3. Thorns are not present on branches;
4. Compatible with peach, apricot, and plum varieties; and
5. Fruits of 'AP3' are smaller than average size, very poor and isolated.

DESCRIPTION OF THE DRAWINGS

The accompanying photographic drawings illustrate the new variety, with the color being as nearly true as is possible with color illustrations of this type.

DETAILED BOTANICAL DESCRIPTION

Figure 1:
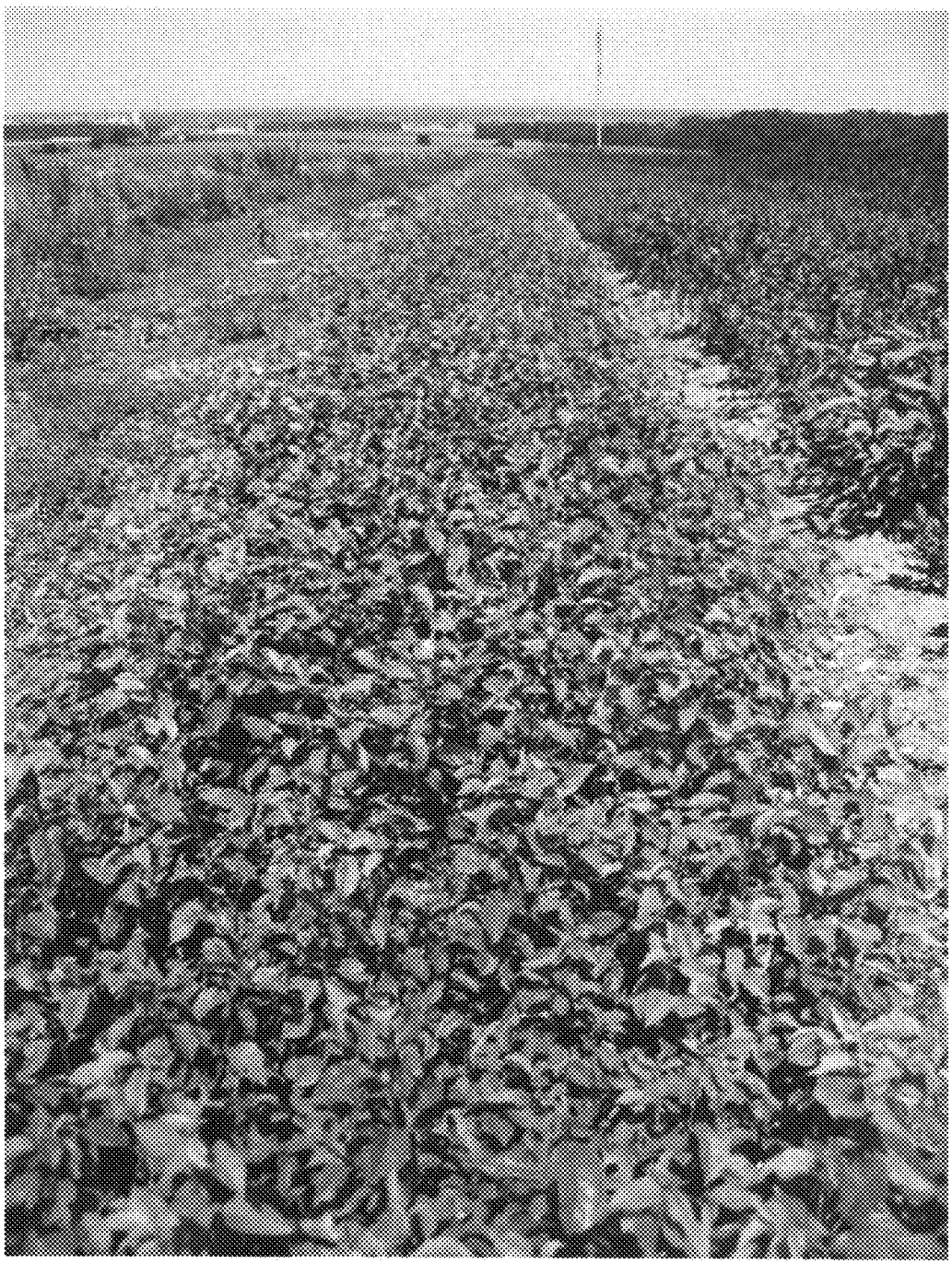
FIG. 1 shows a field of the new variety.
Figure 2:
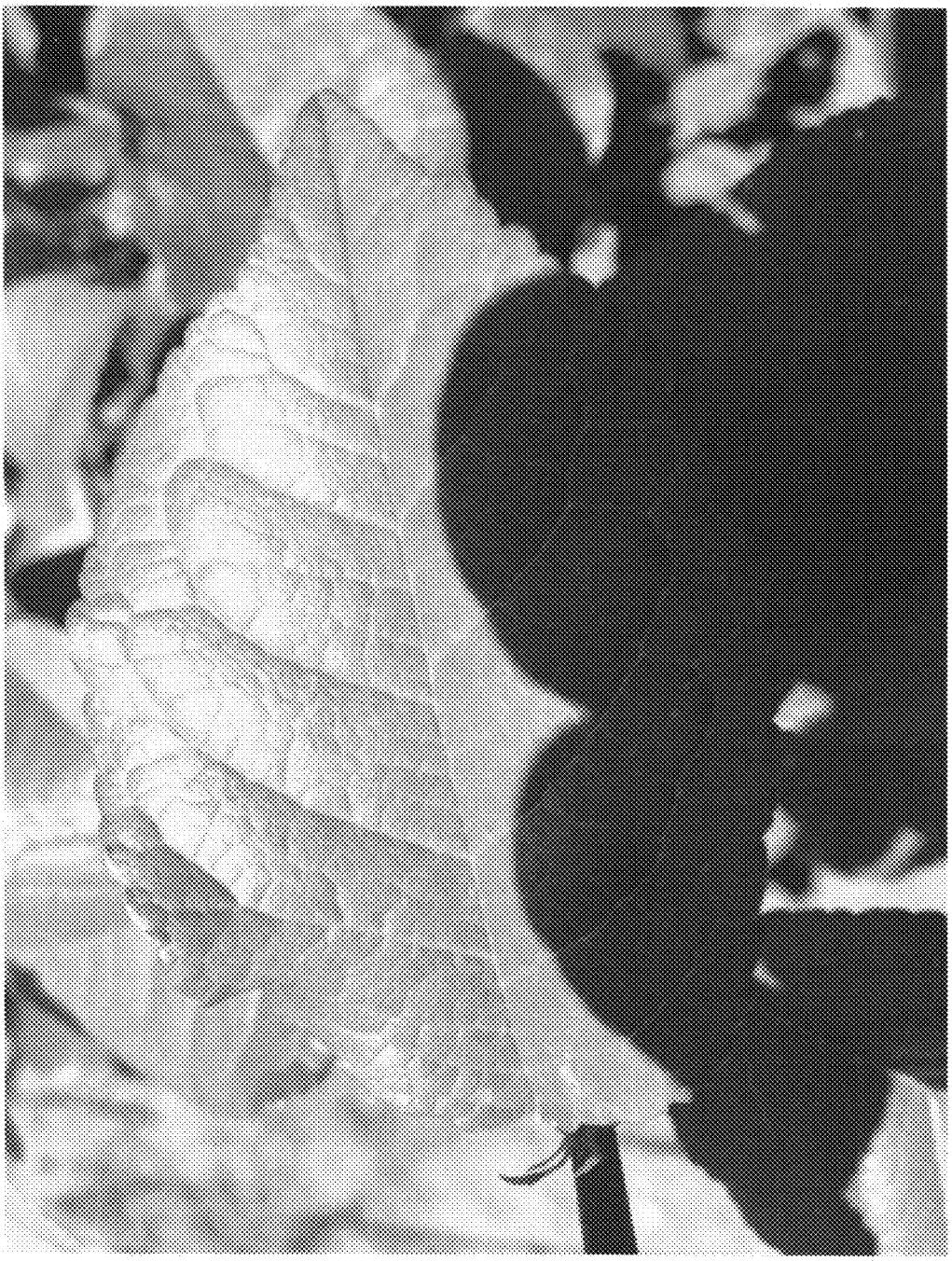
FIG. 2 shows a view of the upper surface of a leaf of the new variety.
Figure 3:
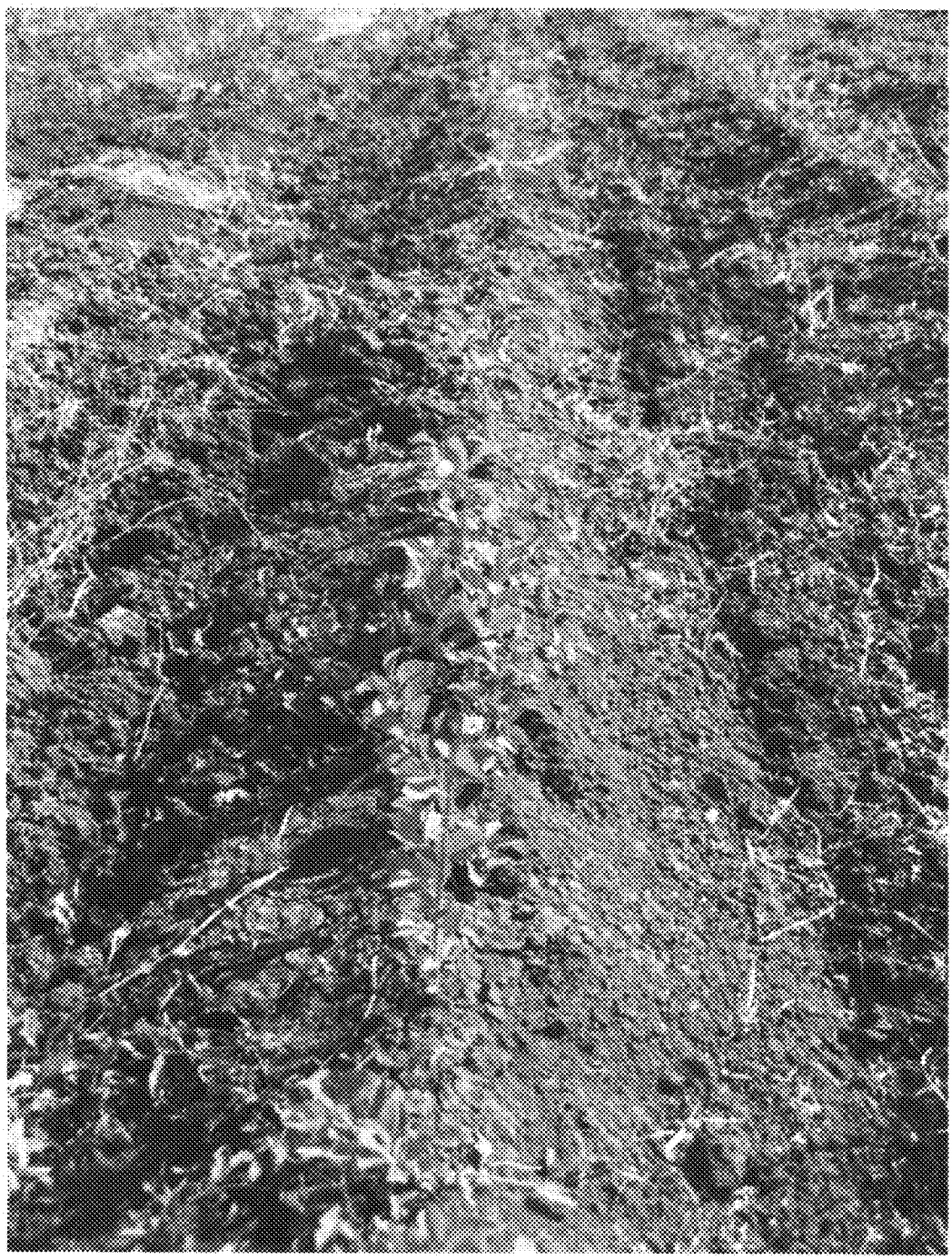
FIG. 3 shows immature plants of the new variety.
Figure 4:
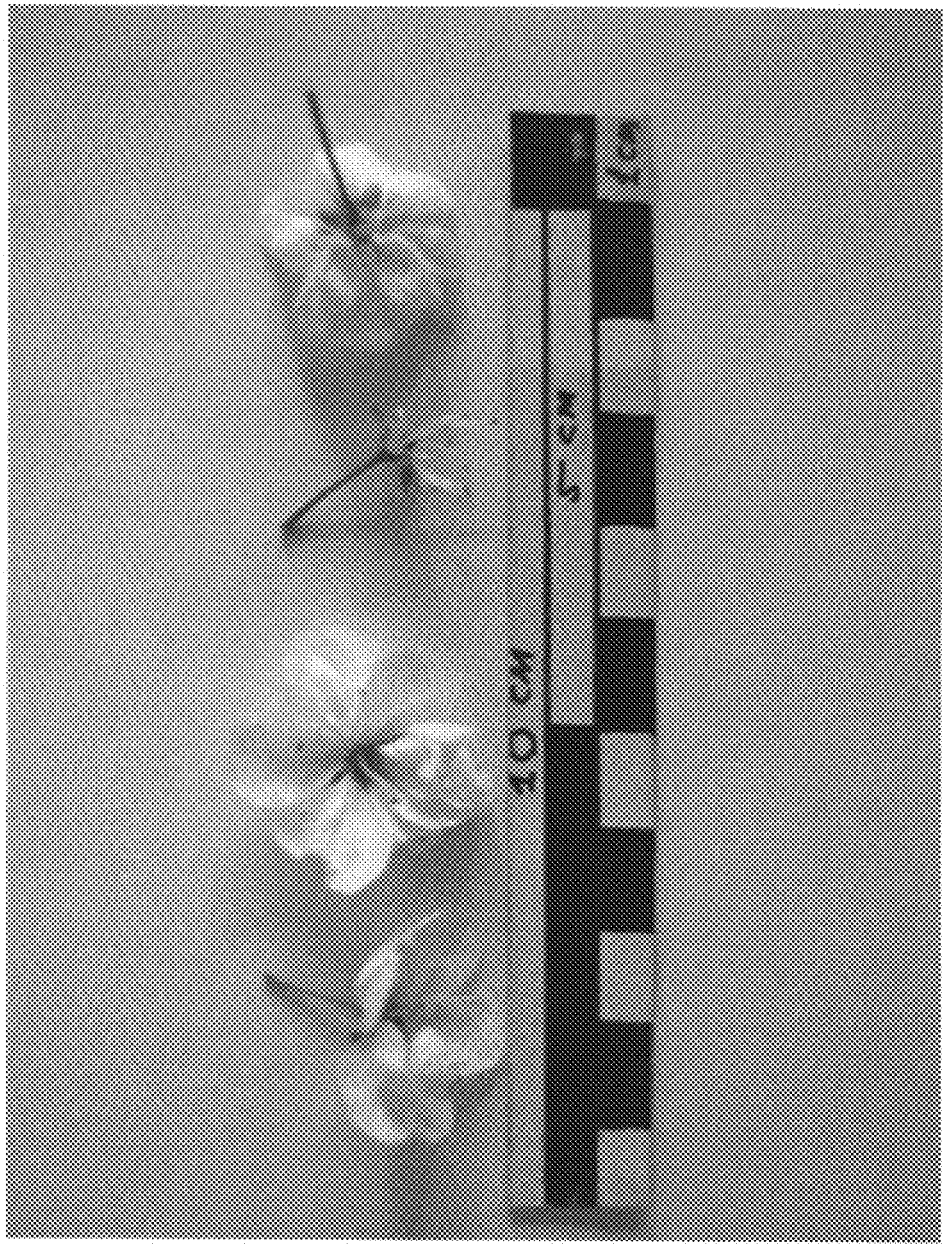
FIG. 4 shows multiple close-up views of flowers of the new variety.
Figure 5:
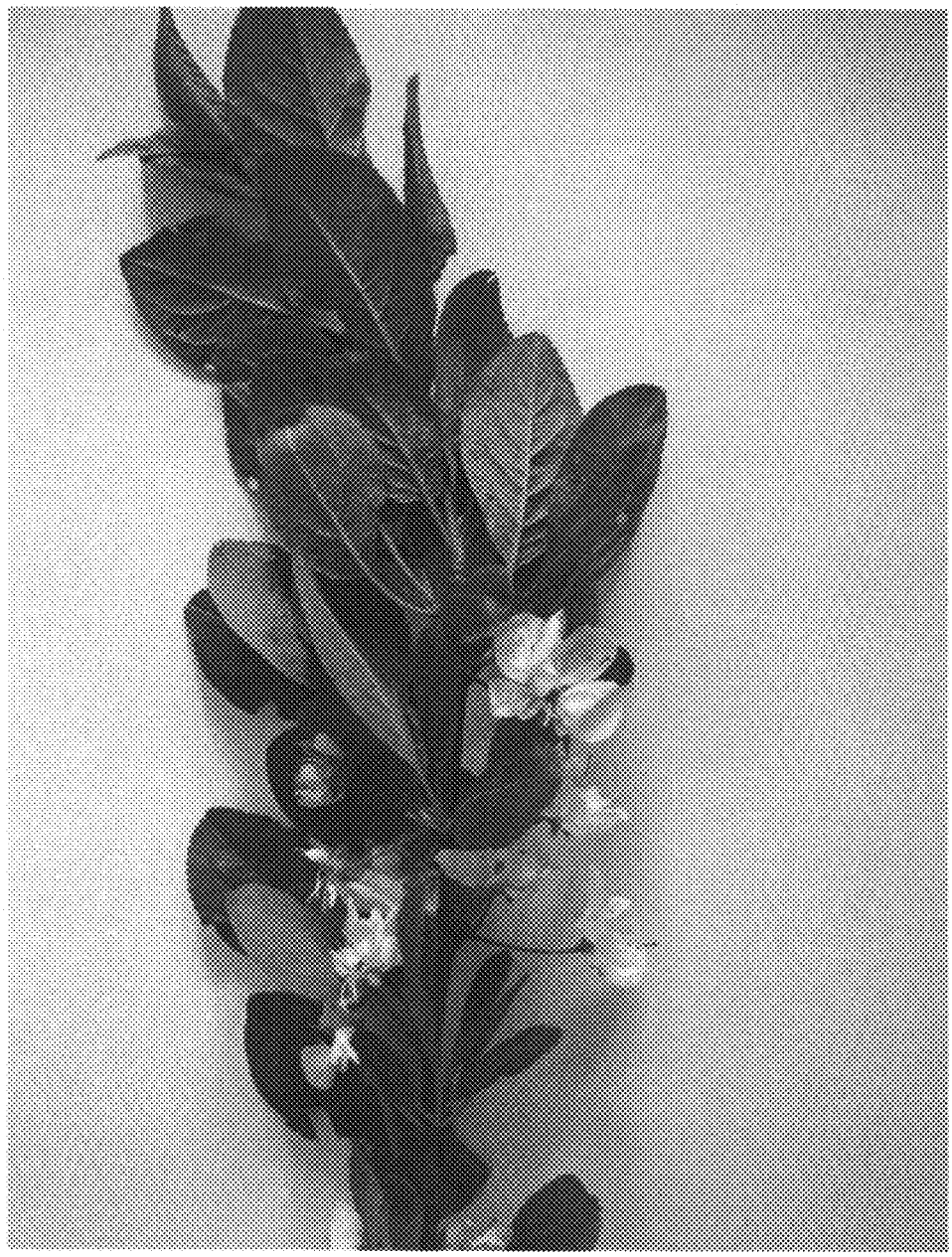
FIG. 5 shows the flowers and leaves of the new variety.
Figure 6:
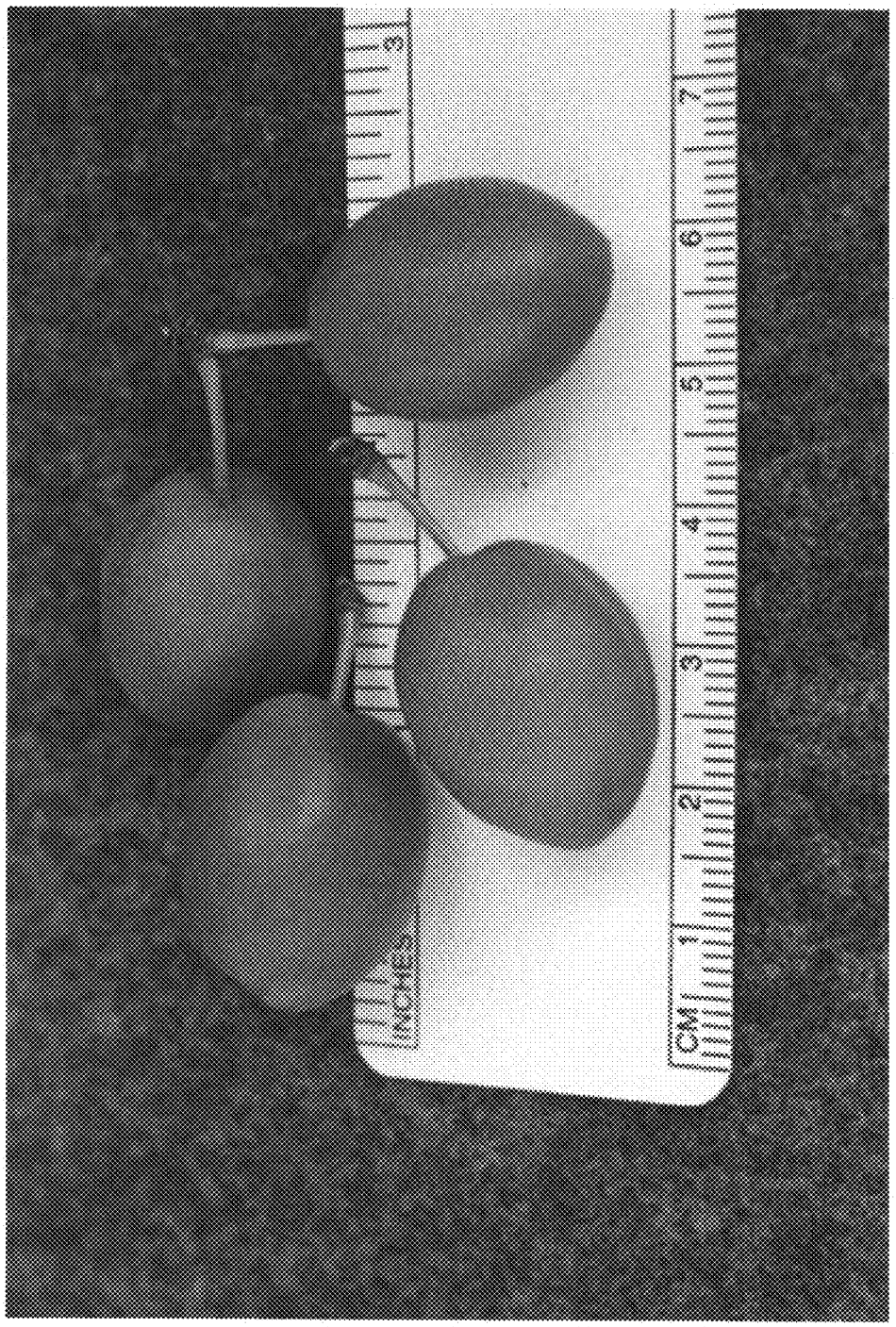
FIG. 6 shows the immature fruit of the new variety.
Figure 7:
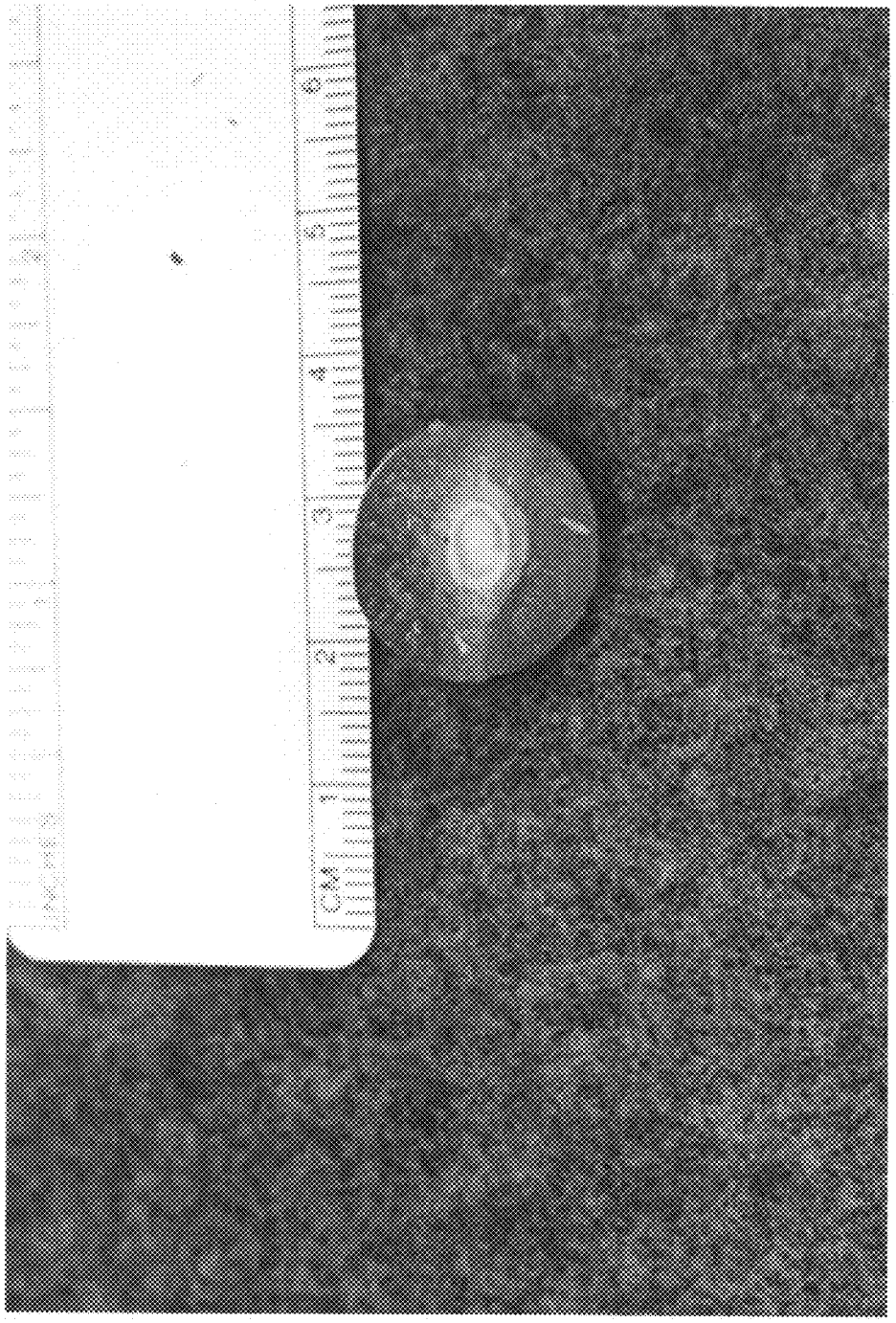
FIG. 7 shows the flesh of the immature fruit of the new variety.
Figure 8:
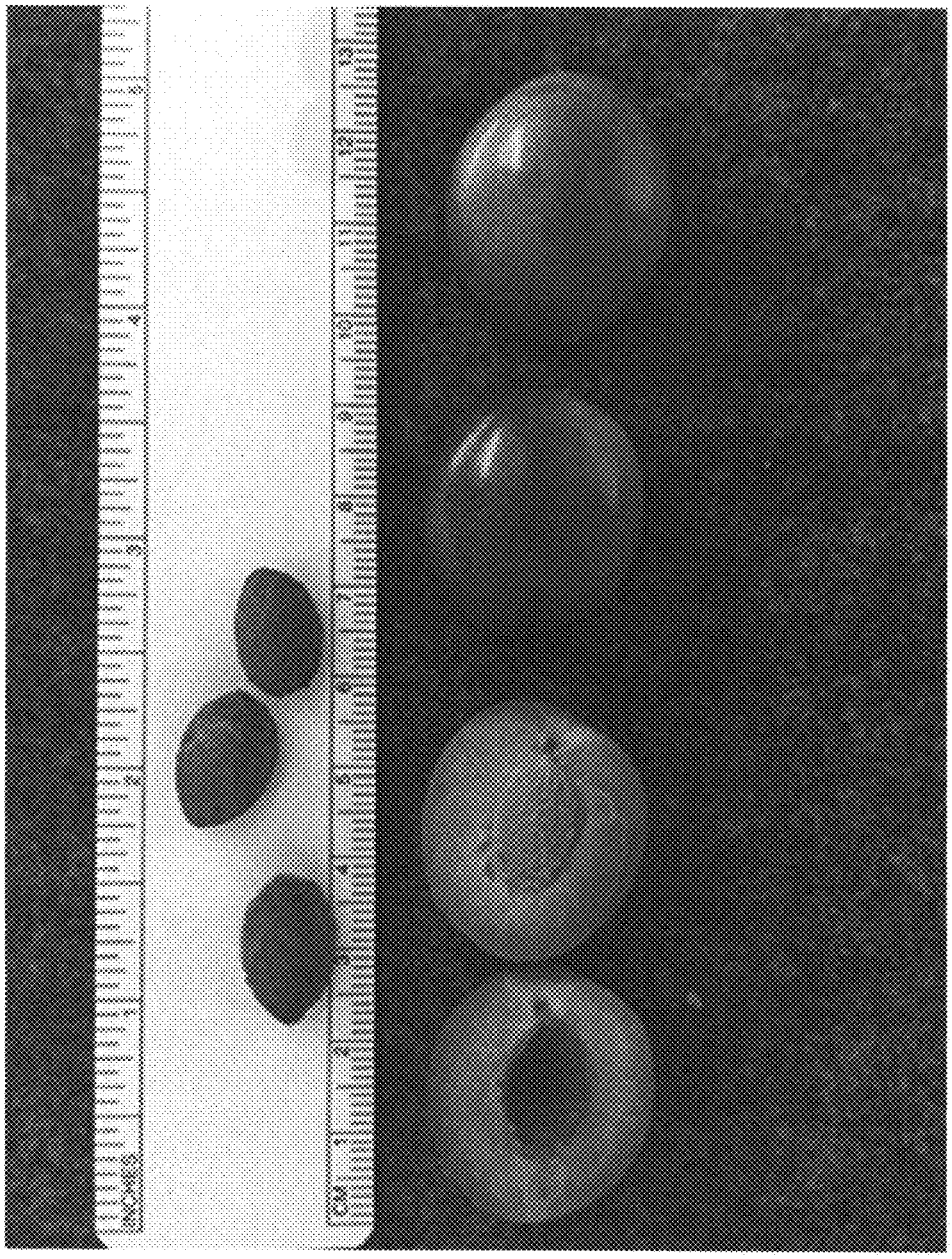
FIG. 8 shows multiple close-up views of the mature fruit and stones of the new variety.

The following detailed description sets forth the characteristics of the new cultivar. The data which defines these characteristics were collected by asexual reproductions via cuttings and slips carried out in Krymsk, Russia. The new variety was grown in a field under warm, dry summer conditions with a temperature range of 70 to 105° F. The winter months are mild with lows to −10° F. The spring and fall months are humid. The plants were treated to regular watering and fertilizer. The color readings were taken in natural daylight. The R.H.S. Colour Chart of The Royal Horticultural Society of London was used for the color references. Plants were 6 years old when described, except where indicated with an asterisk (*), in which case the description was taken on 1-year-old whips.

Tree:

*Use*.—Rootstock.

*Fruit bearing*.—Individual fruits observed.

*Regularity of bearing*.—Annually.

*Type of bearing*.—On spurs and long shoots.

*Tree habit*.—Spreading and upright.

*Number of chilling hours required*.—Approximately 1200.

*Spur length*.—From 1.0 to 5.0 cm.

*Size*.—Height: Average of 5.0 m. Width: Average of 3.0 m.

*Average planting*.—666 trees/hectare.

*Vigor*.—Medium.

*Form*.—Rounded.

*Growth type*.—Medium.

*Trunk*.—Size: 13.0 cm in diameter, measured at 30.0 cm from ground level; approximately 7.3-10.5 cm in width, measured at 20.0 cm from ground level. Color: 148A with 166A one-year old shoots. Surface texture: Smooth. Diameter: 9.0 mm at 3 years when grown in a pot. Texture: Smooth. Lenticels: Length: Average; 0.7 mm. Width: Average; 3.0-5.0 mm. Color*: 163D. Density: Average.

*Branches*.—Diameter: Average; 8.0 to 15.0 mm when measured 10.0 cm from main stem. Surface texture: Smooth. Color* Green; 143C. Form: Direct; without further branching. Average angle: 23°. Lenticels: Length*: Average; 0.8 mm. Width*: Narrow; 0.4 mm. Shape: Elongated. Density*: Numerous; average of 20 lenticels per $cm^2$. Color*: Light brown; 163D. Vegetative bud: Size: 1.5 mm. Shape of apex: Rounded. Position in relation to one year shoot: Adpressed. Arrangement: Slightly deflective.

*Leaves*.—Length*: Average; 100-110.0 mm. Width*: Average; 65.0 mm. Form: Ovoid. Texture: Average. Thickness: Thin. Base: Obtuse. Apex: Acute. Margin: Dentate-crenate. Leaf blade incisions on margin: Bluntly serrate. Pubescence: Light on both surfaces. Surface texture: Upper surface is glossy. Form: Narrow; elliptic. Position of nectaries: Equally on base of leaf blade and on petiole. Color: Upper surface*: Green; 139A. Lower surface*: Green; 138A. Vein: Type: Pinnate. Color: Upper surface: Green; 144B. Lower surface: Light green; 145D. Petiole: Shape: Rounded, with shallow grooves. Length*: Short; 11.3 mm. Diameter*: Average; 1.8 mm. Color*: Green; 145B.

*Flowers*.—Buds: Length: Less than average. Width. Average; 4.0-5.0 mm. Color: Greenish-white. Pedicel: Length: 3.2 cm. Diameter: 1.0-2.0 mm. Color: Green. Bloom time: Mid-April. Pollination required: Yes. Number of flowers per raceme: Numerous. Fragrance: Weak. Petals: Number: 5 per flower. Arrangement: Touching. Shape: Round-oval. Length: 12.0 mm. Width: 11.0 mm. Overall flower diameter: 22.0 mm. Texture: Delicate. Margin: Smooth. Aspect: Wavy. Color: Upper surface: White; N155D. Lower surface: White; N155D. Sepals: Shape: Roundish. Margin: Smooth. Texture: Tight. Length: Average. Width: Average. Color: Upper surface: Green; 146D. Lower surface: Dark green (146B) with a pink (182A) tinge.

*Reproductive organs*.—Pollination requirements: Self-fertile. Anthers: Shape: Rounded. Length: Average. Color: Yellow. Stigma: Shape: Rounded. Color: Brownish-yellow; 165B. Style: Length: Average. Color: Whitish-green; 155C. Stamen number: 28. Pistil length: Stamen level. Pollen: Color: Yellow. Amount: Average.

*Fruit*.—Time of beginning of fruit ripening: Mid-August in Krymsk, Russia. Maturity when described: Small to medium in size. Shape in lateral view: Elliptic and symmetric. Shape of base: Truncate. Shape of apex: Rounded. Depth of fruit stalk cavity: Approximately 2.0-3.0 mm. Depth of fruit suture: Absent to 0.5 mm. Acidity (total titratable acidity): 4.5-5.5%. Fiber content: Very high. Fruit sweetness (Brix): Approximately 14.9-15.1° Brix. Fruit juiciness: Approximately 0.4-0.7% juice. Size: Diameter: 3.2 cm. Length: 3.1 cm. Skin: Thickness: Thin. Texture: Tender. Tendency to crack: None. Mature color: Brownish-red; 187C, including over color. Ground color: Yellow; 145C. Immature color: Yellowish-green; 146C. Presence of bloom: Very weak. Area of fruit over color: 45-80% and somewhat solid with small dots of skin color showing through. Flesh: Aroma: None. Color: Yellowish-green; 146D. Texture: Tender and juicy. Eating quality: Satisfactory (sweet and sour). Stem: Length: Less than 2.0 cm. Width: Thin; 0.1 cm. Color: Green; 144B. Lenticels: Number: One. Appearance: Fine; 0.8-1.2 mm in size. Stone: Number per fruit: 1. Length: 1.5-1.6 cm. Width: 0.9-1.0 cm. Breadth: 0.6-0.7 cm. Form: Rounded. Color: Brown; 164A. Adherence: Free, with no appreciable adherence. Shape in basal view: Acutely prolate ellipsoid. Shape in ventral view: Prolate ellipsoid. Shape in lateral view: Oblong and symmetric. Texture of lateral surfaces: Rough. Width of stalk end: Approximately 1.0-2.0 mm.

Hardiness and tolerance:

*Tree winter hardiness*.—High.

*Low temperature tolerance*.—High; to −35° C.

*Bud winter hardiness*.—High.

*Drought tolerance*.—Higher than average.

Pathogen resistance:

*Fungal disease*.—Resistant to *Monilia cinerea* and *Clasterosporium carpophilum*.

*Other diseases*.—Resistant to *Prunus* pox virus and Root-knot nematodes.

Performance as a rootstock when grafted:

*Root sprouts* (*suckering*).—Resistant to asphyxia.

*Anchorage*.—Average.

*Compatibility*.—Excellent compatibility with plum, apricot, and peach varieties.

*Vigor*.—Medium; Semi-dwarf.

I claim:

1. A new and distinct variety of *Prunus* rootstock plant, as illustrated and described herein.

* * * * *